US011501381B2

United States Patent
Hur et al.

(10) Patent No.: US 11,501,381 B2
(45) Date of Patent: Nov. 15, 2022

(54) METHOD FOR LEARNING AND DEVICE FOR REVIEWING INSURANCE REVIEW CLAIM STATEMENT ON BASIS OF DEEP NEURAL NETWORK

(71) Applicant: LINEWALKS INC., Seoul (KR)

(72) Inventors: Cin Young Hur, Seoul (KR); Yong Hyun Cho, Seoul (KR)

(73) Assignee: LINEWALKS INC., Seoul (KR)

(*) Notice: Subject to any disclaimer, the term of this patent is extended or adjusted under 35 U.S.C. 154(b) by 342 days.

(21) Appl. No.: 16/968,171

(22) PCT Filed: Feb. 21, 2019

(86) PCT No.: PCT/KR2019/002106
§ 371 (c)(1),
(2) Date: Aug. 7, 2020

(87) PCT Pub. No.: WO2019/164284
PCT Pub. Date: Aug. 29, 2019

(65) Prior Publication Data
US 2021/0366049 A1 Nov. 25, 2021

(30) Foreign Application Priority Data
Feb. 23, 2018 (KR) .................. 10-2018-0021885

(51) Int. Cl.
*G06Q 40/08* (2012.01)
*G16H 10/60* (2018.01)
(Continued)

(52) U.S. Cl.
CPC ............... *G06Q 40/08* (2013.01); *G06N 3/08* (2013.01); *G16H 10/60* (2018.01); *G16H 20/10* (2018.01); *G16H 50/20* (2018.01)

(58) Field of Classification Search
CPC .................................... G06Q 50/20–26
See application file for complete search history.

(56) References Cited

U.S. PATENT DOCUMENTS

2003/0069760 A1* 4/2003 Gelber .................. G06Q 10/10
705/2
2008/0091705 A1* 4/2008 McBride ................ G06Q 50/10
707/999.102
(Continued)

FOREIGN PATENT DOCUMENTS

JP 2001-184411 A 7/2001
JP 2004-355381 A 12/2004
(Continued)

OTHER PUBLICATIONS

International Search Report of PCT/KR2019/002106 dated Jun. 7, 2019 from Korean Intellectual Property Office.

*Primary Examiner* — Neal Sereboff
(74) *Attorney, Agent, or Firm* — Revolution IP, PLLC (57) ABSTRACT

A method for learning an insurance claim statement on a basis of a deep neural network, includes: receiving, by an insurance claim statement reviewing device, an input of a plurality of insurance review claim statements containing at least one of first information, second information, third information and fourth information; classifying, by the insurance claim statement reviewing device, the general items, the diagnosed patient injury/disease items, the treatment history items, or the prescription items; converting, by the insurance claim statement reviewing device, the categorical data or the numerical data; inputting, by the insurance claim statement reviewing device, the converted data; training, by the insurance claim statement reviewing device, the deep neural network using training data of the converted data; and verifying, by the insurance claim statement reviewing device, the deep neural network using verification data of the converted data.

5 Claims, 5 Drawing Sheets

(51) Int. Cl.
    *G16H 50/20*    (2018.01)
    *G16H 20/10*    (2018.01)
    *G06N 3/08*     (2006.01)

(56) References Cited

U.S. PATENT DOCUMENTS

2012/0185275 A1* 7/2012 Loghmani .............. G06Q 40/08
                                                    705/3
2017/0337334 A1* 11/2017 Stanczak ................ G06Q 30/04
2019/0371438 A1* 12/2019 Chintamaneni ........ G16H 40/20
2021/0134430 A1*  5/2021 Mason ................... G06Q 40/02

FOREIGN PATENT DOCUMENTS

| JP | 2005-275595 A    | 10/2005 |
|----|------------------|---------|
| JP | 2008-134756 A    | 6/2008  |
| KR | 10-2017-0008444 A | 1/2017 |
| KR | 10-2017-0014866 A | 2/2017 |

* cited by examiner

| | Medical care benefit cost | |
|---|---|---|
| Type | medical outpatient | |
| receiver | | |
| | | 1 General Item |
| | disease | |
| | high blood pressure | W/20 |
| | | 2 Diagnosed Patient Injury/ Disease Item |

3 Treatment History Item

| First Visit | | NO | CODE | CLASS | PRICE | UNIT | ..... | ..... | ..... | ..... | ..... |
|---|---|---|---|---|---|---|---|---|---|---|---|
| | | | | | | | 4 Prescription Issuance Item | | | | |

METHOD FOR LEARNING AND DEVICE FOR REVIEWING INSURANCE REVIEW CLAIM STATEMENT ON BASIS OF DEEP NEURAL NETWORK

TECHNICAL FIELD

The present disclosure relates to a method for learning and a device for reviewing an insurance review claim statement on the basis of a deep neural network. More specifically, the present disclosure relates to a technique for constructing a deep neural network structure in accordance with the characteristics of an insurance review claim statement, and a technique for learning the review performance of a reviewing device at an expert level.

BACKGROUND ART

Lives of individuals are endlessly threatened by unpredictable diseases and accidents. Insurance does not actively prevent occurrence of these diseases and accidents, but passively aims to meet the economic demands resulting from occurrence of accidents. In order to achieve this goal, many people form an insurance group to prepare for the risk of occurrence of unexpected accidents, and pay money in advance in the form of insurance premiums to form a common property, and can receive money in insurance when members of the group have accidents.

In this modern society where insurance is generalized, the number of acts of obtaining insurance and the number of submissions of insurance review claim statements for insurance coverage through the insurance plan are rapidly increasing, and each claim statement is becoming very complicated and diversified. For reference, there are various insurances such as accident insurance and health insurance. In order to receive the insurance claim amount for such insurance, an insurance review claim statement should be submitted to the insurance company or the review and assessment service.

Every insurance application form submitted to obtain insurance or every submitted insurance review claim statement should be reviewed by persons, and therefore reviewing the same highly depends on persons and the amount of reviews by a person is large. Accordingly, the accuracy of a person's review may be low, and there is a big variation in accuracy among the reviewers. In addition, while the standards for insurance review are regularly changed, review by a person can make it slow to cope with the change and, thereby obstructing accurate and precise review of an insurance review claim statement.

In order to address such issues, Korean Patent Application Publication No. 10-2017-0014866 (Feb. 8, 2017) has been disclosed. However, the prior art technology is merely intended to lower the dependence on humans in terms of obtaining insurance, and has not disclosed anything about processing the insurance review claim statement. Nor have prior art techniques disclosed evaluating an insurance review claim statement by utilizing an artificial intelligence deep learning architecture.

DISCLOSURE

Technical Problem

It is an object of the present disclosure to provide a method for learning and a device for reviewing an insurance review claim statement on the basis of a deep neural network.

Technical Solution

In accordance with one aspect of the present disclosure, provided is a method for learning, by an insurance claim statement reviewing device, an insurance claim statement on a basis of a deep neural network, the method including receiving an input of a plurality of insurance review claim statements containing at least one of first information including a plurality of general items related to general details of the insurance claim statements, second information including a plurality of diagnosed patient injury/disease items related to an injury or a disease of a diagnosed patient, third information including a plurality of treatment history items related to a treatment history, and fourth information including a plurality of prescription issuance items related to prescription issuance; classifying the general items, the diagnosed patient injury/disease items, the treatment history items, or the prescription items included in the first to fourth information in the insurance claim statements into categorical data or numerical data, converting the categorical data or the numerical data so as to be input to a deep neural network learning unit; inputting the converted data to the deep neural network learning unit in the insurance claim statement reviewing device; training the deep neural network using a first part of the converted data; and verifying the deep neural network using a second part of the converted data.

In the converting, when the data constituting the general items, the diagnosed patient injury/disease items, the treatment history items, or the prescription issuance items corresponds to a specific category as the categorical data, a value for identifying the specific category may be input to an element mapped to the specific category, wherein the categorical data for each of the items may be configured in an array having as many elements as the number of possible categories, wherein each of the elements may be mapped to the specific category.

When the data constituting the general items, the diagnosed patient injury/disease items, the treatment history items, or the prescription issuance items are specific numerical values as the numerical data, the converting may include normalizing the numerical values considering a maximum, minimum, average, and standard deviation of each of the numerical values.

The first information may have a one-to-many relationship with the second to fourth information, wherein the inputting may include inputting the converted second to fourth information to a recurrent neural network learning unit.

The receiving may include dividing the input of the insurance review claim statements into a predetermined size.

The verifying may include calculating possibility of reconciliation of the insurance review claim statements and deriving a first result; receiving an actual reconciliation result of the insurance claim statements from an expert review information provider in the insurance claim statement reviewing device; calculating an error between the first result and the actual reconciliation result; updating a neural network weight based on the calculated error to reduce the error; suppressing overfitting of the updated neural network based on the second part; and when the calculated error is less than or equal to a predetermined value, terminating the learning method.

In accordance with another aspect of the present disclosure, provided is a device for reviewing an insurance claim statement on a basis of a deep neural network, the device including a data collector configured to receive an input of a plurality of insurance review claim statements containing at least one of first information including a plurality of general items related to general details of the insurance claim statements, second information including a plurality of diagnosed patient injury/disease items related to an injury or a disease of a diagnosed patient, third information including a plurality of treatment history items related to a treatment history, and fourth information including a plurality of prescription issuance items related to prescription issuance; a data converter configured to classify the general items, the diagnosed patient injury/disease items, the treatment history items, or the prescription items included in the first to fourth information in the insurance claim statements into categorical data or numerical data, convert the categorical data or the numerical data so as to be input to a deep neural network learning unit, and input the converted data to the deep neural network learning unit; and the deep neural network learning unit configured to train the deep neural network using a first part of the converted data; and verify the deep neural network using a second part of the converted data.

The device may further include a reconciliation possibility output unit configured to calculate possibility of reconciliation of the insurance review claim statements and derive a first result; and an expert review information provider configured to provide an actual reconciliation result of the insurance claim statements, wherein the deep neural network learning unit may be configured to calculate an error between the first result and the actual reconciliation result; update a neural network weight based on the calculated error to reduce the error; suppress overfitting of the updated neural network based on the second part; and terminate a method for learning the insurance claim statement when the calculated error is less than or equal to a predetermined value.

Advantageous Effects

According to an embodiment of the present disclosure, a method for learning and a device for reviewing an insurance review claim statement on the basis of a deep neural network may be provided.

BEST MODE

As the present disclosure allows for various changes and numerous embodiments, particular embodiments will be illustrated in the drawings and described in detail in the following description. However, this is not intended to limit the present disclosure to specific embodiments, but is intended to cover all modifications, equivalents, and substitutes within the spirit and scope of the present disclosure. In the following description of the present disclosure, a detailed description of related known technology may be omitted to avoid obscuring the subject matter of the present disclosure.

Terms such as first and second may be used in describing various components, but the components should not be limited by the terms. The terms are used only for the purpose of distinguishing one component from another.

Terms used in this specification are merely adopted to explain specific embodiments, and are not intended to limit the present disclosure. A singular expression includes a plural expression unless the two expressions are contextually different from each other. In this specification, the term "include" or "have" is intended to indicate that characteristics, figures, steps, operations, constituents, and components disclosed in the specification or combinations thereof exist. The term "include" or "have" should be understood as not pre-excluding possibility of existence or addition of one or more other characteristics, figures, steps, operations, constituents, components, or combinations thereof.

REFERENCE NUMERALS

100: Insurance claim statement reviewing device
110: Deep neural network learning unit
120: Data collector
130: Data converter
140: Threshold setter
150: Expert review information provider
160: Reconciliation possibility output unit

MODE FOR INVENTION

Hereinafter, embodiments according to the present disclosure will be described in detail with reference to the accompanying drawings. In the following description with reference to the accompanying drawings, the same or like elements are assigned the same reference numerals and redundant description thereof will be omitted.

In addition, terms such as first and second used below are merely identification symbols for distinguishing the same or corresponding components, and the same or corresponding components are not limited by the terms such as first and second.

In addition, the term combination will be used as a concept covering not only a direct physical contact between the components, but also a contact between components with another component interposed therebetween in terms of the contact relationship between the components.

Regarding a computer program, the suffixes "module" and/or "unit" for a component may be a part of a computer program for operating the computer as a means of a specific function, or may be a part of a computer program for realizing a specific function in the computer. For example, module A can be interpreted as a computer program for operating the computer as means A or a computer program for realizing function A in the computer. In a method, a "step" may be implemented as a computer program on a computer and executed. In addition, "modules" and/or "units" may be combined to form a "group".

An application refers to a set of computer programs designed to perform a specific task, and is also called an application program. A user may add related functions by installing an application according to an embodiment of the present disclosure on his or her electronic device.

An electronic device of the user on which the application is installed is composed of CPU, RAM, ROM, and a storage device as in a computer, a tablet, and a smartphone, and may be provided with an environment in which the entire system is controlled through a graphical operating system such as Windows, iOS, Android, and Linux. In particular, the environment is specialized for smartphones capable of sending and receiving calls and texts by registered contacts.

The flowcharts in the drawings attached herein are merely for explanation of the disclosure, and are not necessarily flowcharts to be perfectly implemented without a bug on a computer.

A terminal mentioned herein may be a typical user terminal such as a smartphone, a personal computer, or a tablet.

Figure 1:
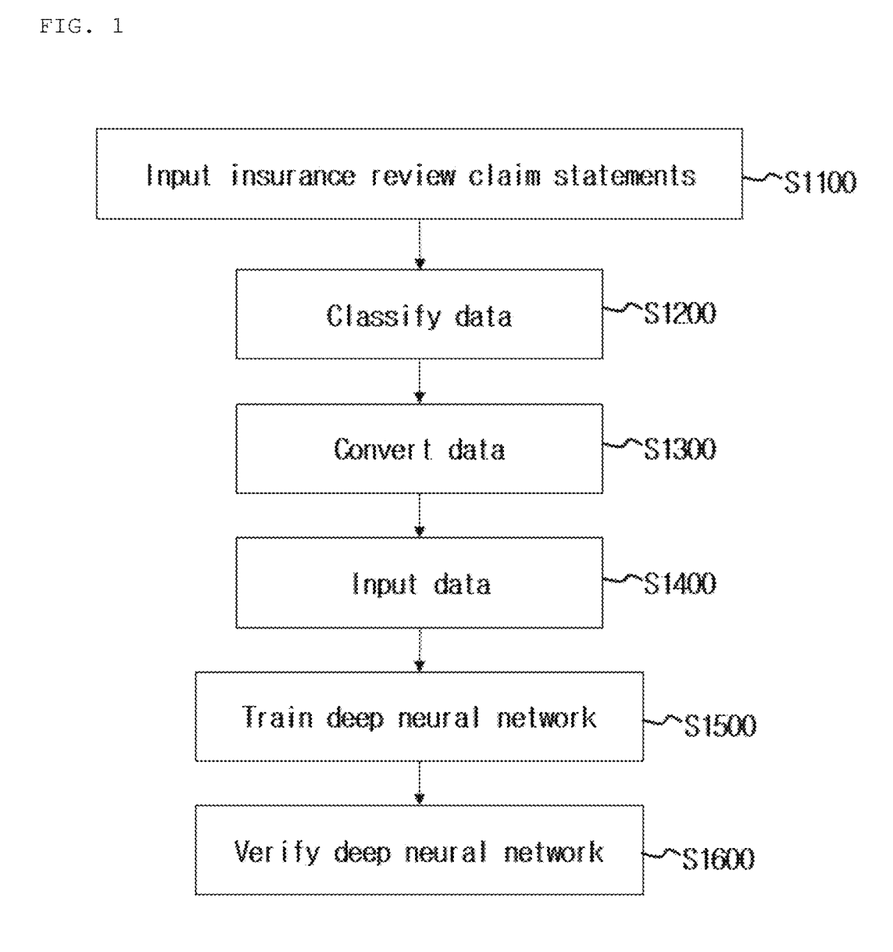
FIG. 1 is a flowchart illustrating an operation according to the present disclosure.

FIG. 1 is a flowchart illustrating an operation according to the present disclosure. Referring to FIG. 1, the operation, performed by a device for reviewing an insurance claim statement, includes receiving an input of a plurality of insurance review claim statements containing at least one of first information including a plurality of general items related to general details of the insurance claim statements, second information including a plurality of diagnosed patient injury/disease items related to an injury or a disease of a diagnosed patient, third information including a plurality of treatment history items related to a treatment history, and fourth information including a plurality of prescription issuance items related to prescription issuance (S1100); classifying, into categorical data or numerical data, the general items, diagnosed patient injury/disease items, treatment history items, or prescription items included in the first to fourth information in the insurance claim statements (S1200); converting the categorical data or the numerical data so as to be input to a deep neural network learning unit (S1300); inputting the converted data to the deep neural network learning unit in the device for reviewing an insurance claim statement (S1400); training a deep neural network using a first part of the converted data (S1500); and verifying the deep neural network using a second part of the converted data (S1600). The above steps will be described in detail one by one.

Figure 2:
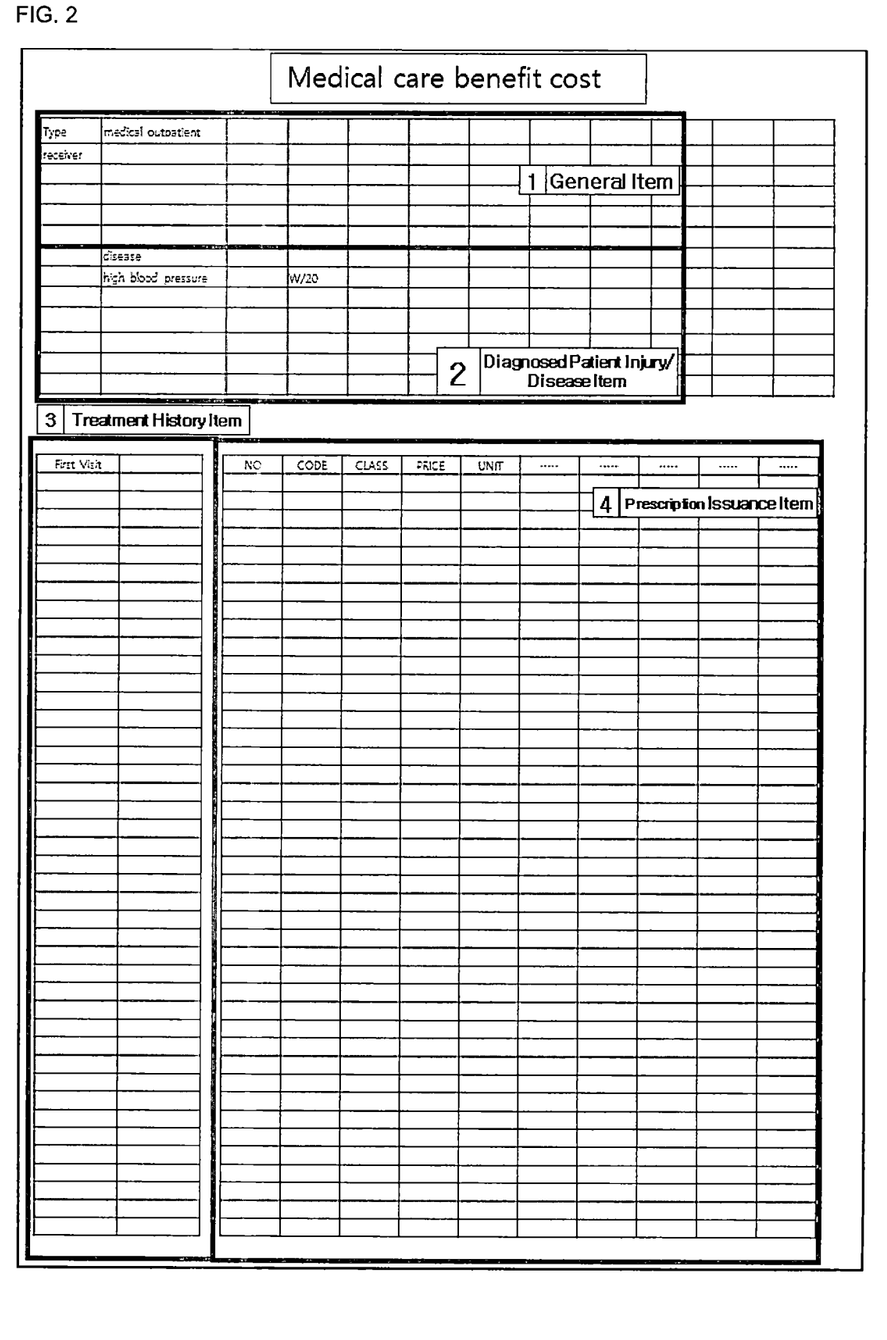
FIG. 2 shows an insurance review claim statement.

Initially, the insurance claim statement reviewing device receives receiving an input of a plurality of insurance review claim statements containing at least one of first information including a plurality of general items related to general details of an insurance claim statement, second information including a plurality of diagnosed patient injury/disease items related to an injury or a disease of a diagnosed patient, third information including a plurality of treatment history items related to a treatment history, and fourth information including a plurality of prescription issuance items related to prescription issuance. More specifically, the insurance review claim statement generally contains general items related to the statement, diagnosed patient injury/disease items, treatment history items, and prescription issuance items. FIG. 2 shows such an insurance review claim statement. The general items may contain general content of the insurance review claim statement, such as a patient's name and social security number, the name and code of a nursing home, the name and code of a coverage agency, the type of insurance, the date of receipt, the route of arrival, whether the patient is in charge, the type of treatment, and the signature of the insurance policy holder. Next, the diagnosed patient injury/disease items may include items related to an injury or a disease of a diagnosed patient. It may contain all details related to a disease, such as the name and portion of the injury or disease, a disease classification code, an operation status, an examination subject, a specialized subject, an injury, a specific code, a care start date, the number of care days, and a result of treatment. Next, the treatment history items may contain details of a medical service provided to the patient. Next, the prescription issuance items may contain information about medicines prescribed for the patient in or out of the hospital. More specifically, they may contain a code, a classification name, a product name, a unit price, a single dose, a daily dose, a total dose, and a cost. As described above, the insurance review claim statement reviewing device receives an input of an insurance claim statement containing one or more of the first to fourth information. A large number of insurance claim statements may be stored in a remote storage. The form of storing may be a data lake based on a distributed file system or may be a large database system.

Next, the insurance review claim statement reviewing device may classify, into categorical data or numerical data, the general items, diagnosed patient injury/disease items, treatment history items, or prescription items included in the first to fourth information in the insurance review claim statements. More specifically, the first to fourth information contained in the insurance review claim statements may be classified into categorical or numerical data. For example, the disease code, medical practice code, and main ingredient code may be categorical data. That is, regarding the disease code, diabetes is mapped to E11, and cholera is mapped to A00. Regarding the medical practice code, the medical free of the first examination is mapped to AA100, and a drug and toxicology test is mapped to C4501010. Regarding the main ingredient code of medicine, an anti-malignant tumor agent is mapped to C4501010. In this way, when the types are limited as in the case of diseases, medical practice, or main ingredients of medicine (for example, in the case of diseases, all diseases ranging from cold to AIDS), they are defined as categorical data. In addition, various codes may be mapped to the respective categories.

Figure 3:
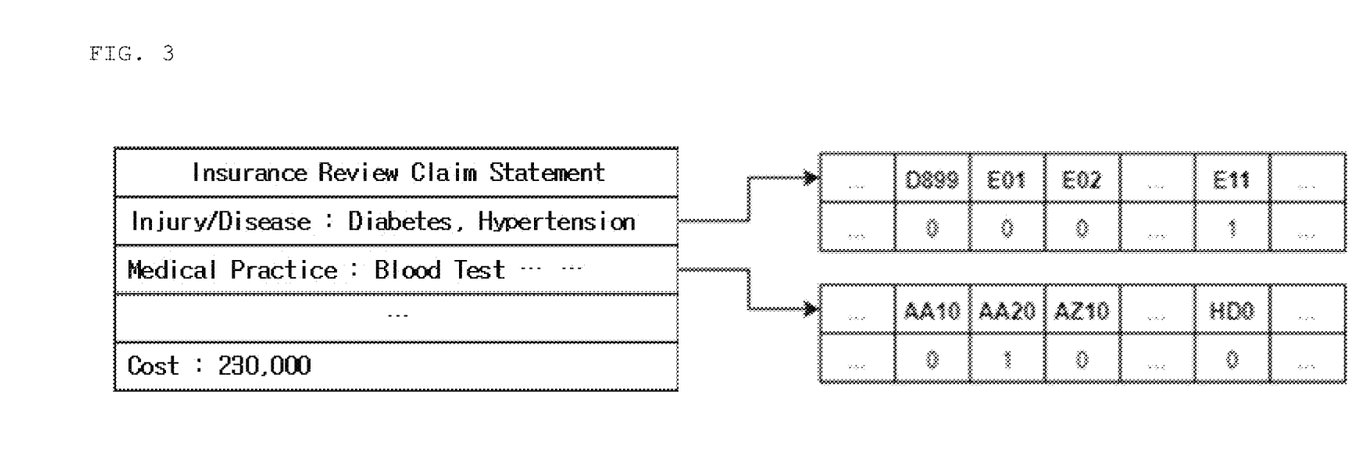
FIG. 3 is a conceptual diagram of conversion of categorical data according to the present disclosure.

In addition, when the data constituting the general items, the diagnosed patient injury/disease items, the treatment history items, or the prescription issuance items corresponds to a specific category as the categorical data, a value for identifying the specific category may be input to an element mapped to the specific category. In this case, the categorical data for each item may be configured in an array having as many elements as the number of possible categories, and each of the elements may be mapped to the specific category. More specifically, for the categorical data among the general items, the diagnosed patient injury/disease items, the treatment history items, or the prescription issuance items, when the number of all values each item can have is n, the categorical data for each item may be configured in a one-dimensional array of n elements. For example, in the case of the injury/disease items, when the number of injury/disease items, such as cold, headache, and cancer, is 1,000, an array with a thousand elements may be placed in one category, and a code value (e.g., an injury/disease code) may be mapped to each element. For example, when a patient's disease is diabetes, an identifiable value such as '1' may be input to the corresponding element (an element corresponding to E11), and an identifiable value such as '0' may be input to the elements (other than E11) to which the other diseases that the patient is not suffering from are mapped. The identifiable values can be input in the opposite way, and are not limited to the '1' and '0'. In other words, an array is configured by filing the elements corresponding to diabetes with '1' and all the other elements with '0'.

The array may be composed of two or more arrays. More specifically, for example, one array may be configured with the elements from A00 to J99, and another array may be configured with the elements from K00 to U99.

When the data constituting the general items, the diagnosed patient injury/disease items, the treatment history items, or the prescription issuance items are specific numerical values as the numerical data, the numerical values may be normalized considering the maximum, minimum, average, and standard deviation of each of the numerical values. For example, among the injury/disease items, the number of days of care is an item in which a number can be actually input. The number of days of care in a first insurance claim statement may be 10 days, the number of days of care in a second insurance claim statement may be 20 days, the number of days of care in a third insurance claim statement may be 5 days, and the number of days of care in another insurance review claim statement may be a different number of days. As described above, the number of days of care may differ among various insurance review claim statement. By collecting these data, calculating the maximum, minimum, median, average, and standard deviation, normalizing the same, relative comparison may be allowed.

The data converted in this way may be input to the deep neural network learning unit within the insurance claim statement reviewing device. At this time, not all the converted data may be input to the reviewing device. Instead, only a part of the data may be input to train the deep neural network, and the remaining part may be input later to verify the training level of the trained deep neural network. Hereinafter, the neural network training and verification operations will be described in detail.

Figure 4:
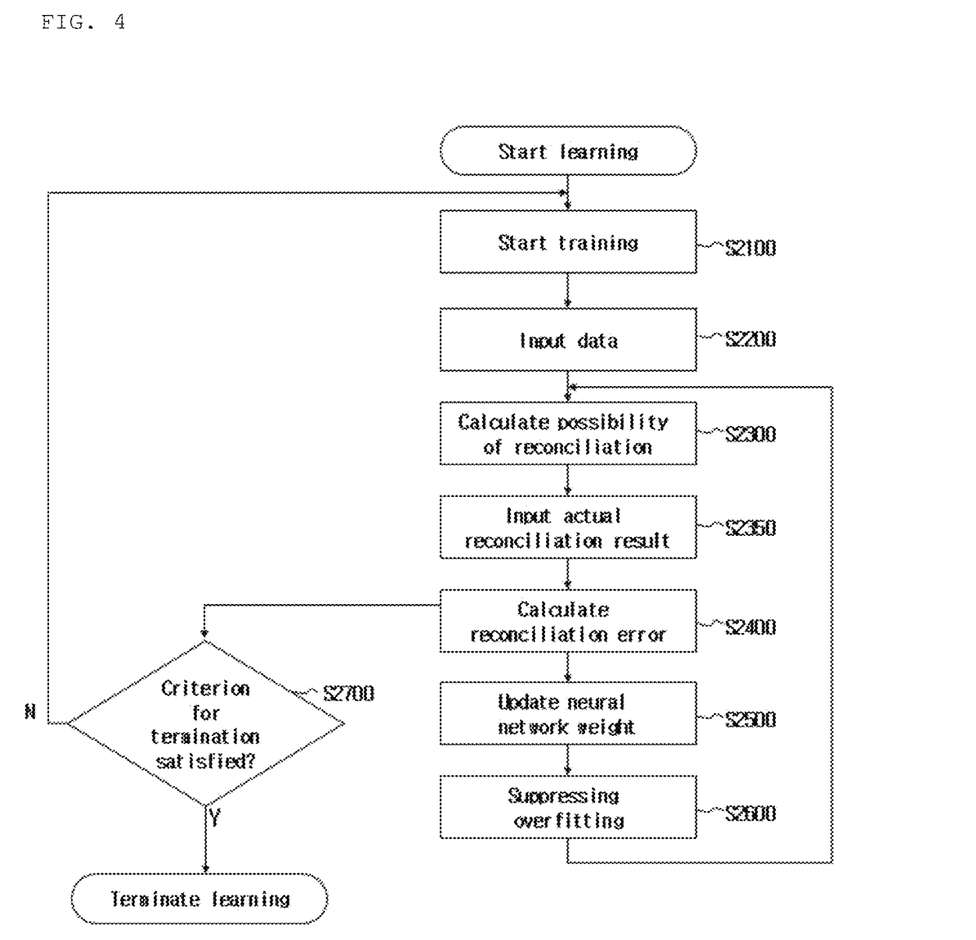
FIG. 4 is a flowchart illustrating a verification process according to the present disclosure.

FIG. 4 is a flowchart illustrating a verification process according to the present disclosure. Referring to FIG. 4, the verifying may include calculating possibility of reconciliation of the insurance review claim statements and deriving a first result; receiving an actual reconciliation result of the insurance claim statements from an expert review information provider in the insurance claim statement reviewing device; calculating an error between the first result and the actual reconciliation result; updating a neural network weight based on the calculated error to reduce the error; suppressing overfitting of the updated neural network based on the second part; and when the calculated error is less than or equal to a predetermined value, terminating the learning method.

More specifically, deep neural network learning is started. Specifically, training of the deep neural network is started (S2100). To this end, the classified and converted data is input to the deep neural network learning unit (S2200). An insurance review claim statement learning device calculates the possibility of reconciliation of the insurance review claim statement (S2300). Here, the possibility of reconciliation means the possibility that the input insurance statement fails in the review for various reasons (e.g., false claims, unfair claims, excessive claims, erroneous claims, etc.). The actual reconciliation result of the insurance review claim statement is provided from the expert review information provider (S2350). The reconciliation result is the result of review of the various submitted insurance review claim statements (e.g., pass or fail). The error between the possibility of reconciliation and the actual reconciliation result is calculated (S2400). Based on the obtained error, a neural network weight is updated so as to reduce the error (S2500). When the error is reduced, the deep neural network may be overfitted. Accordingly, an operation of suppressing the overfitting may be further performed (S2600). More specifically, some of the given data may be used as training data, and the remaining data may be divided into verification data. Thus, the deep neural network is trained through the training data, and then trained with the verification data to suppress overfitting of the deep neural network. The ratio between the training data and the verification data is not predetermined and may be determined according to the user setting. After the overfitting is resolved, the operations are repeated, starting with the procedure of calculating the possibility of reconciliation of the insurance claim statement. When the error between the possibility of reconciliation and the actual reconciliation result is less than or equal to a value set by the user, it is checked whether a criterion for terminating the training and the verification is satisfied (S2700).

The possibility of reconciliation may be calculated by the following equation.

$$\text{Possibility of reconciliation} = \frac{1}{1+e^{-ax}} \quad \text{(Equation 1)}$$

The equation above is a sigmoid function, and is used for an output value, which changes according to an input value of each node in the deep neural network. 'x' denotes the input value and 'a' denotes a slope. When the input value is significant, a large value close to 1 is output. When the input value is insignificant, a small value close to 0 is output. The output value closer to 1 corresponds to higher possibility of reconciliation, and the output value closer to 0 corresponds to lower possibility of reconciliation. That is, if the possibility of failing in the review is high, a value close to 1 is obtained. Otherwise, a value close to 0 is obtained.

The error between the possibility of reconciliation and the actual reconciliation result may be obtained using cross-entropy, mean square error, and the like. In an embodiment, an error between a deep neural network review result and a review result from an actual review expert may be obtained through a cross-entropy error. The cross-entropy error may be calculated by the following equation.

$$E = -\frac{1}{N}\sum_n\sum_k t_{nk}\log y_{nk} \quad \text{(Equation 2)}$$

Here, yk is the output from the deep neural network, and tk is a review result of provided by the expert examination information provider, which is obtained through a review by a human. tk is 1 only for an element of the index corresponding to a correct answer, and is 0 for the other elements, which is an estimated logarithmic value when reviewing is actually performed by a person. Therefore, the output for the correct answer (directly review by a person) determines the total value of the cross-entropy error. Thus, when the output corresponding to the correct answer increases, the error value becomes closer to 0. Conversely, when the output corresponding to the correct answer decreases, the error value increases. The sum of loss function for all the training data may be obtained.

The neural network weight may be updated to reduce the error is as much as possible. The weight may be updated using various methods such as stochastic gradient descent (SGD), momentum, RMSprop, and Adaptive Moment Estimation (Adam). For example, the momentum may apply inertia to the process of updating the weight to make an additional movement to a certain degree based on the remembered past movement, thereby quickly updating the weight.

The first information may have a one-to-many relationship with the second to fourth information. In the inputting operation, the converted second to fourth information may be input to a recurrent neural network learning unit. More specifically, in the insurance claim statements, the general items may have a one-to-many relationship with the other items. For example, one patient may suffer from several diseases, and may thus receive various types of medical treatment and receive various types of prescriptions. For example, patient A may have 5 cases of diagnosed patient injury/disease, 10 cases of treatment history, and 10 details of prescription issuance, and patient B may have 2 cases of diagnosed patient injury/disease, 5 cases of treatment history, and 10 details of prescription issuance. In this way, the number of the diagnosed patient injury/disease items, treatment history items, prescription issuance items may differ among patients or insurance review claim statements. This point should be taken into consideration in inputting the data to the neural network. In this regard, a recurrent neural network capable of responding appropriately regardless of the length of the input data may be utilized.

In other words, the first information corresponding to the general items in the statement may be input to a feedforward neural network at one time, and the second to fourth information corresponding to the other items may be consecutively input. When the consecutive data is input, the second to fourth information may be input by utilizing a recurrent neural network having an effect of remembering the initially input data. Methods of inputting the second to fourth information having a plurality of records may include randomly mixing and inputting the information in any order, unidirectional inputting in the forward or reverse direction, and bi-directional inputting applying both forward inputting and reverse inputting.

The error may be reduced through the weight updating or the like. Excessive reduction of the error may be may be suitable for the given training data, but may increase an error for new data (verification data or actual data). This may mean that the updating is not suitable for a variety of general-purpose data. In other words, the overfitting represents a state in which even the noise of the training data is learned, and it is preferable to stop learning before the deep neural network learns even such noise, such that deep neural network versatility is provided. As described above, in order to suppress the overfitting, predetermined data among given data is used as verification data, that is, data for suppressing the overfitting. A predetermined ratio among predetermined data for suppressing the overfitting may be adjusted by the user.

In addition, the receiving may further include dividing the input of the insurance review claim statements into a predetermined size. More specifically, a predetermined amount of insurance review claim statement data may be input to the deep neural network, and learning may be performed by dividing the entire training data into small training data.

The method may further include testing the deep neural network after the verification operation is completed. Testing the deep neural network is determined based on the degree to which the review result of the deep neural network is consistent with the review result from the expert. More specifically, specific insurance review claim statements are reviewed through an insurance review claim statement learning device using a deep neural network that has been trained and verified. The learning device may generate an alarm or the like for an insurance review claim statement that excessively claims insurance. In addition, a tag such as normal may be attached to an insurance review claim statement that normally claims insurance. As described above, the learning device may determine whether the insurance review claim statement is normal or abnormal, and determine, through comparison, the degree of agreement between the result determining normal or abnormal and the review result by an expert who actually reviews the insurance review claim statement to evaluate the performance of the learning device. For such test evaluation, evaluation measures such as precision, recall, f1, AUC, and MCC may be used.

Figure 5:
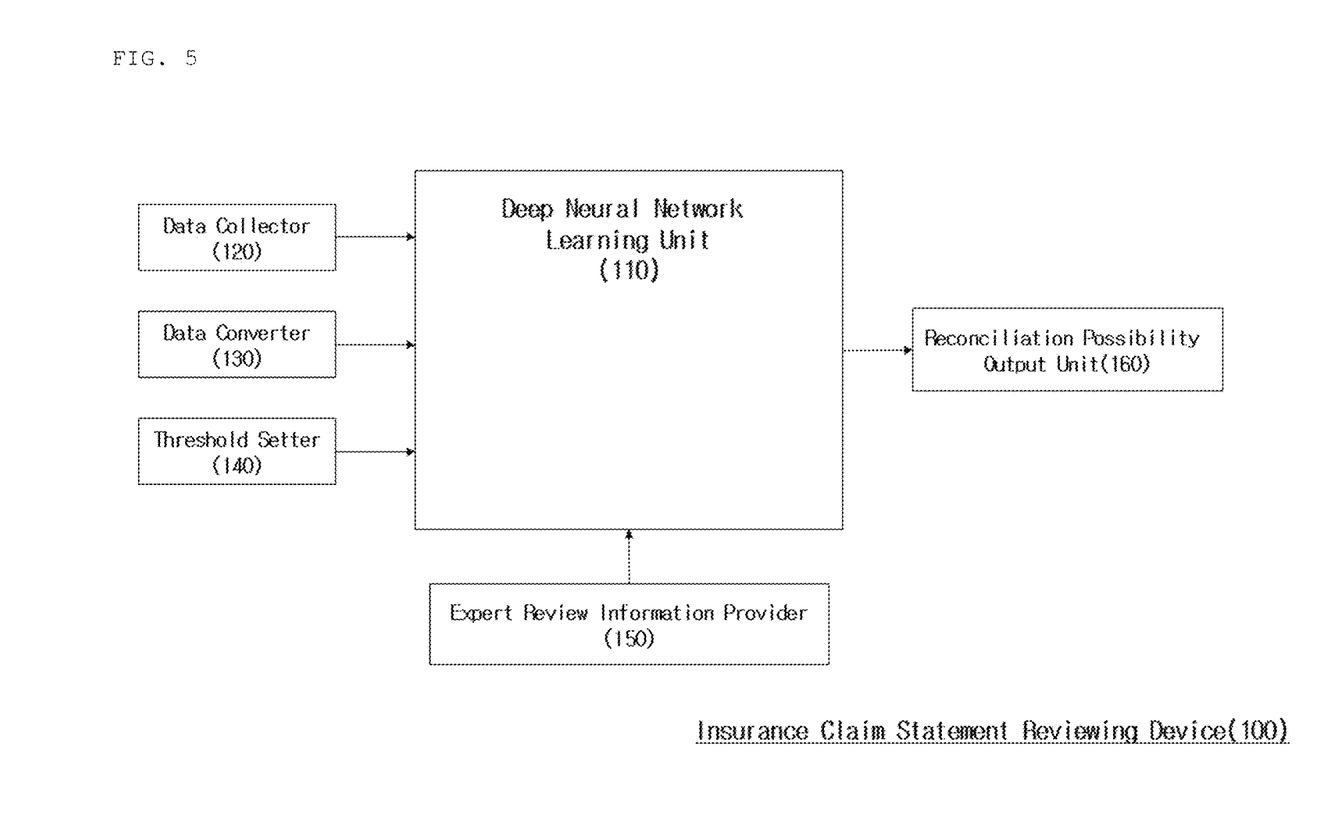
FIG. 5 is a block diagram showing a device for reviewing an insurance claim statement according to the present disclosure.

FIG. 5 is a block diagram showing a device for reviewing an insurance claim statement according to the present disclosure. Description will be given with reference to FIG. 5, and descriptions of parts described above will be omitted.

The device for reviewing an insurance claim statement on a basis of a deep neural network includes a data collector 120 configured to receive an input of a plurality of insurance review claim statements containing at least one of first information including a plurality of general items related to general details of the insurance claim statements, second information including a plurality of diagnosed patient injury/disease items related to an injury or a disease of a diagnosed patient, third information including a plurality of treatment history items related to a treatment history, and fourth information including a plurality of prescription issuance items related to prescription issuance; a data converter 130 configured to classify the general items, the diagnosed patient injury/disease items, the treatment history items, or the prescription items included in the first to fourth information in the insurance claim statements into categorical data or numerical data, convert the categorical data or the numerical data so as to be input to a deep neural network learning unit, and input the converted data to the deep neural network learning unit; and the deep neural network learning unit 110 configured to train the deep neural network using a first part of the converted data, and verify the deep neural network using a second part of the converted data. The insurance review claim statement reviewing device may be installed and operated together with the existing review system, or may be installed and operated separately. Further, according to the hardware specification of the reviewing device, the amount of the insurance claim statement data to be reviewed may be adjusted in the memory. For details of the data collector and the data converter, refer to the description given above in relation to the method invention.

The threshold refers to a value given when the deep neural network improves the performance of reviewing an insurance claim statement through learning and verification, or an error rate falls within a specific range. The threshold may be adjusted by the user through a threshold setter. If the threshold is set to be low, the insurance claim statement reviewing device may strongly simulate the input data. Otherwise, the reviewing device may roughly simulate the input data. That is, the intensity of the simulation is adjusted. In addition, when the error fluctuates within the threshold as in the case where the error decreases and then increases or increases and then decreases, the deep neural network learning unit may stop training and verification.

Through the method for learning and device for reviewing insurance review claim statements on the basis of a deep neural network as described above, the insurance review claim statements may be evaluated as when evaluated by a real expert. Thereby, accident-related insurance fraud or systematic and intelligent false claims or excessive claims by medical workers or the like may be filtered out in advance. In addition, the insurance payment reviewing system may be advanced and automated.

In addition, through the present disclosure, a general model with review knowledge may be created by training a deep neural network-based model with a large number of insurance review claim statements. Further, this model may be reused and specialized for different cases. For example, a reviewing model specialized in reviewing a specific disease, a model specialized in reviewing for respective hospital types (hospital, general hospital, advanced general hospital), or a model specialized in a region such as a metropolitan/farm/fishing village may be created. Such a model may be applied to a reviewing device for detailed cases.

The method and processing described above are instructions to be executed by, for example, a processor, a controller, or other processing devices and may be encoded or stored in a compact disk read-only memory (CD-ROM), a magnetic disk, an optical disc, a flash memory, a random access memory (RAM) or read only memory (ROM), an erasable programmable read only memory (EPROM), or other machine-readable or computer-readable media.

Such a medium may be implemented by an instruction executable system, apparatus, or device, or any device that contains, stores, communicates, propagates, or moves executable instructions for use in connection therewith. Alternatively or additionally, the method and processing may be implemented by analog or digital logic using hardware such as one or more integrated circuits, or one or more processor executable instructions; or by software of functions defined as an application programming interface (API), a dynamic link library (DLL), a local or remote procedure call or available in a shared memory; or by a combination of hardware and software.

In other implementations, the method may be represented by a signal or radio-signal medium. For example, the instructions for implementing the logic of any given program may take the form of an electrical, magnetic, optical, electromagnetic, infrared or other type of signal. The system described above may receive these signals through a communication interface, such as a fiber optic interface, an antenna, or another analog or digital signal interface, restore instructions from the signals, store the instructions in a machine-readable memory, and/or execute the same using a processor.

In addition, the present invention may be implemented in hardware or software. The invention may also be implemented as computer-readable code on a computer-readable recording medium. The computer-readable recording medium includes all kinds of recording devices in which data that may be read by a computer system is stored. Examples of computer-readable recording media include ROM, RAM, CD-ROM, magnetic tapes, floppy disks, and optical data storage devices, and also include carrier-wave type implementation (e.g., transmission over the Internet). The computer-readable recording medium may be distributed to a computer system connected over a network, and computer-readable code may be stored and executed thereon in a distributed manner. Functional programs, code, and code segments for implementing the method described above may be easily inferred by programmers in the art to which the embodiments pertain.

Embodiments of the present disclosure may include a carrier wave having electronically readable control signals that may be operated with a programmable computer system on which one of the methods described herein is executed. Embodiments of the disclosure may be implemented as a computer program product having program code, the program code being operated to execute one of the methods when the computer program is run on a computer. The program code may be stored on, for example, a machine-readable carrier. One embodiment of the disclosure may be a computer program having program code for executing one of the methods described herein when the computer program is run on a computer. The disclosure may include a computer or a programmable logic device for performing one of the methods described above. Programmable logic devices (e.g., field programmable gate arrays, complementary metal oxide semiconductor based logic circuits) may be used to perform some or all of the functions described above.

Although an embodiment of the present disclosure has been described above, it is apparent to those skilled in the art that various modifications and changes can be made to the present disclosure by adding, changing, or deleting components within the scope not departing from the spirit of the present disclosure as set forth in the claims. Such modifications and changes are also within the scope of the present disclosure.

INDUSTRIAL APPLICABILITY

As suggested by the present disclosure, the present invention can be used for various insurance reviews based on a deep neural network through learning as if an actual insurance inspector processes insurance review claim statements.

The invention claimed is:

1. A method for learning an insurance claim statement on a basis of a deep neural network, the method comprising:
   receiving, by an insurance claim statement reviewing device, an input of a plurality of insurance review claim statements containing at least one of:
   first information including a plurality of general items related to general details of the insurance claim statements;
   second information including a plurality of diagnosed patient injury/disease items related to an injury or a disease of a diagnosed patient;
   third information including a plurality of treatment history items related to a treatment history; and
   fourth information including a plurality of prescription issuance items related to prescription issuance;
   classifying, by the insurance claim statement reviewing device, the general items, the diagnosed patient injury/disease items, the treatment history items, or the prescription items included in the first to fourth information in the insurance claim statements into categorical data or numerical data;
   converting, by the insurance claim statement reviewing device, the categorical data or the numerical data so as to be input to a deep neural network learning unit;
   inputting, by the insurance claim statement reviewing device, the converted data to the deep neural network learning unit in the insurance claim statement reviewing device;
   training, by the insurance claim statement reviewing device, the deep neural network using training data of the converted data; and
   verifying, by the insurance claim statement reviewing device, the deep neural network using verification data of the converted data,
   wherein the verifying comprises:
      calculating, by the insurance claim statement reviewing device, possibility of reconciliation of the insurance review claim statements and deriving a first result;
      receiving, by the insurance claim statement reviewing device, an actual reconciliation result of the insurance claim statements from an expert review information provider in the insurance claim statement reviewing device;

calculating, by the insurance claim statement reviewing device, an error between the first result and the actual reconciliation result;

updating, by the insurance claim statement reviewing device, a neural network weight based on the calculated error to reduce the error;

suppressing, by the insurance claim statement reviewing device, overfitting of the updated neural network based on the verification data; and when the calculated error is less than or equal to a predetermined value, terminating, by the insurance claim statement reviewing device, the learning method.

2. The method of claim 1, wherein, in the converting, when the data constituting the general items, the diagnosed patient injury/disease items, the treatment history items, or the prescription issuance items corresponds to a specific category as the categorical data, a value for identifying the specific category is input to an element mapped to the specific category, wherein the categorical data for each of the items is configured in an array having as many elements as the number of possible categories, wherein each of the elements is mapped to the specific category.

3. The method of claim 1, wherein, when the data constituting the general items, the diagnosed patient injury/disease items, the treatment history items, or the prescription issuance items are specific numerical values as the numerical data, the converting comprises:

normalizing the numerical values considering a maximum, minimum, average, and standard deviation of each of the numerical values.

4. The method of claim 1, wherein the first information has a one-to-many relationship with the second to fourth information, wherein the inputting comprises:

inputting, by the insurance claim statement reviewing device, the converted second to fourth information to a recurrent neural network learning unit.

5. The method of claim 1, wherein the receiving comprises:

dividing, by the insurance claim statement reviewing device, the input of the insurance review claim statements into a predetermined size.

* * * * *